United States Patent
Birchard et al.

(10) Patent No.: US 9,919,131 B2
(45) Date of Patent: *Mar. 20, 2018

(54) MAGNETICALLY GUIDED CATHETER WITH CONCENTRIC NEEDLE PORT

(71) Applicant: BIOSENSE WEBSTER, INC., Irvine, CA (US)

(72) Inventors: Christopher J. Birchard, Newport Beach, CA (US); Jerett A. Creed, Miami, CA (US); Wai Chung Wong, Chino Hills, CA (US)

(73) Assignee: Biosense Webster, Inc., Irvine, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 14/697,520

(22) Filed: Apr. 27, 2015

(65) Prior Publication Data

US 2015/0238731 A1    Aug. 27, 2015

Related U.S. Application Data

(60) Continuation of application No. 13/846,904, filed on Mar. 18, 2013, now Pat. No. 9,017,283, which is a
(Continued)

(51) Int. Cl.
*A61M 25/01*    (2006.01)
*A61M 25/00*    (2006.01)
(Continued)

(52) U.S. Cl.
CPC ......... *A61M 25/0127* (2013.01); *A61B 5/042* (2013.01); *A61B 5/06* (2013.01);
(Continued)

(58) Field of Classification Search
CPC .......... A61M 25/0067; A61M 25/0082; A61M 25/0084; A61M 25/0089; A61M 25/01;
(Continued)

(56) References Cited

U.S. PATENT DOCUMENTS 3,605,742 A    9/1971 Tibbs
3,941,130 A    3/1976 Tibbs
(Continued)

FOREIGN PATENT DOCUMENTS

EP    0 447 216 A1    9/1991
WO    WO 99/59663    11/1999
(Continued)

OTHER PUBLICATIONS

International Search Report and Written Opinion of the International Searching Authority dated Sep. 5, 2008 for International Application No. PCT/US2008/064652 (7 pages).
(Continued)

*Primary Examiner* — Nathan R Price
*Assistant Examiner* — Justin L Zamory
(74) *Attorney, Agent, or Firm* — Lewis Roca Rothgerber Christie LLP

(57) ABSTRACT

A catheter for ablation, mapping, injection, and directional control by an external magnetic system has a catheter body, an intermediate section, and a tip section having a tip electrode with an omnidirectional distal end and a concentric needle port. The tip electrode houses a magnetic device and a position sensor in an integrated configuration that facilitates a path in the tip section for extension and retraction of a component, including an injection needle, with reduced stress and friction. The integrated configuration is an efficient use of space in the tip electrode that allows the tip section to carry both the position sensor and the necessary volume of magnetic or magnetizable material to accomplish magnetic navigation. The catheter also includes a very soft and flexible intermediate section and an even softer and more flexible distal transitional section carrying additional magnetic members to facilitate remote magnetic navigation.

20 Claims, 14 Drawing Sheets

Related U.S. Application Data division of application No. 12/125,903, filed on May 22, 2008, now Pat. No. 8,480,653.

(60) Provisional application No. 60/939,649, filed on May 23, 2007.

(51) Int. Cl.

| | | |
|---|---|---|
| *A61B 5/06* | (2006.01) | |
| *A61B 18/14* | (2006.01) | |
| *A61B 5/042* | (2006.01) | |
| *A61B 34/00* | (2016.01) | |
| *A61B 17/00* | (2006.01) | |
| *A61B 18/00* | (2006.01) | |
| *A61B 90/00* | (2016.01) | |
| *A61B 34/20* | (2016.01) | |

(52) U.S. Cl.
CPC .......... *A61B 5/062* (2013.01); *A61B 18/1492* (2013.01); *A61B 34/73* (2016.02); *A61M 25/008* (2013.01); *A61M 25/0068* (2013.01); *A61M 25/0082* (2013.01); *A61M 25/0084* (2013.01); *A61M 25/0158* (2013.01); *A61B 2017/00084* (2013.01); *A61B 2018/00839* (2013.01); *A61B 2034/2051* (2016.02); *A61B 2090/3975* (2016.02); *A61M 25/0069* (2013.01); *A61M 2025/0089* (2013.01)

(58) Field of Classification Search
CPC .......... A61M 25/0127; A61M 25/0136; A61M 25/0158; A61M 2025/0166; A61M 2025/09183
See application file for complete search history.

(56) References Cited

U.S. PATENT DOCUMENTS

| | | |
|---|---|---|
| 4,108,177 A | 8/1978 | Pistor |
| 4,228,802 A | 10/1980 | Trott |
| 4,391,199 A | 7/1983 | Morin |
| 5,176,647 A | 1/1993 | Knoepfler |
| 5,217,441 A | 6/1993 | Shichman |
| 5,380,292 A | 1/1995 | Wilson |
| 5,478,316 A | 12/1995 | Bitdinger et al. |
| 5,480,387 A | 1/1996 | Gabriel et al. |
| 5,688,243 A | 11/1997 | Rammler |
| 5,938,603 A | 8/1999 | Ponzi et al. |
| 5,997,509 A | 12/1999 | Rosengart et al. |
| 6,123,699 A | 9/2000 | Webster, Jr. |
| 6,126,647 A | 10/2000 | Posey et al. |
| 6,165,164 A | 12/2000 | Hill et al. |
| 6,171,277 B1 | 1/2001 | Ponzi |
| 6,183,463 B1 | 2/2001 | Webster, Jr. |
| 6,201,387 B1 | 3/2001 | Govari |
| 6,254,573 B1 | 7/2001 | Haim et al. |
| 6,309,370 B1 | 10/2001 | Haim et al. |
| 6,321,106 B1 | 11/2001 | Lemelson |
| 6,385,472 B1 | 5/2002 | Hall et al. |
| 6,484,118 B1 | 11/2002 | Govari |
| 6,540,725 B1 | 4/2003 | Ponzi |
| 6,575,931 B1 | 6/2003 | Ponzi |
| 6,623,474 B1 | 9/2003 | Ponzi |
| 6,802,824 B2 | 10/2004 | Mickley et al. |
| 6,905,476 B2 * | 6/2005 | Ponzi .................. A61M 25/008 604/264 |
| 6,980,843 B2 | 12/2005 | Eng et al. |
| 7,300,438 B2 | 11/2007 | Falwell et al. |
| 7,399,294 B2 | 7/2008 | Mickley |
| 8,079,982 B1 | 12/2011 | Ponzi et al. |
| 2003/0117888 A1 | 6/2003 | Reilly et al. |
| 2003/0195491 A1 | 10/2003 | Schneider et al. |
| 2003/0233076 A1 | 12/2003 | Mickley et al. |
| 2004/0039338 A1 | 2/2004 | Lee et al. |
| 2004/0204672 A1 | 10/2004 | Palasis et al. |
| 2005/0038390 A1 | 2/2005 | Fago et al. |
| 2005/0234337 A1 | 10/2005 | Browne |
| 2009/0018497 A1 | 1/2009 | Birchard et al. |
| 2009/0099513 A1 | 4/2009 | Birchard |
| 2009/0099514 A1 | 4/2009 | Birchard et al. |

FOREIGN PATENT DOCUMENTS

| | | |
|---|---|---|
| WO | WO 02/30554 A2 | 4/2002 |
| WO | WO 2004/014533 A1 | 2/2004 |
| WO | WO 2005/077441 A2 | 8/2005 |

OTHER PUBLICATIONS

International Search Report and Written Opinion of the International Searching Authority dated Sep. 8, 2008 for International Application No. PCT/US2008/064661 (6 pages).

International Search Report dated Sep. 9, 2008 for International Application No. PCT/US2008/064667 (4 pages).

* cited by examiner

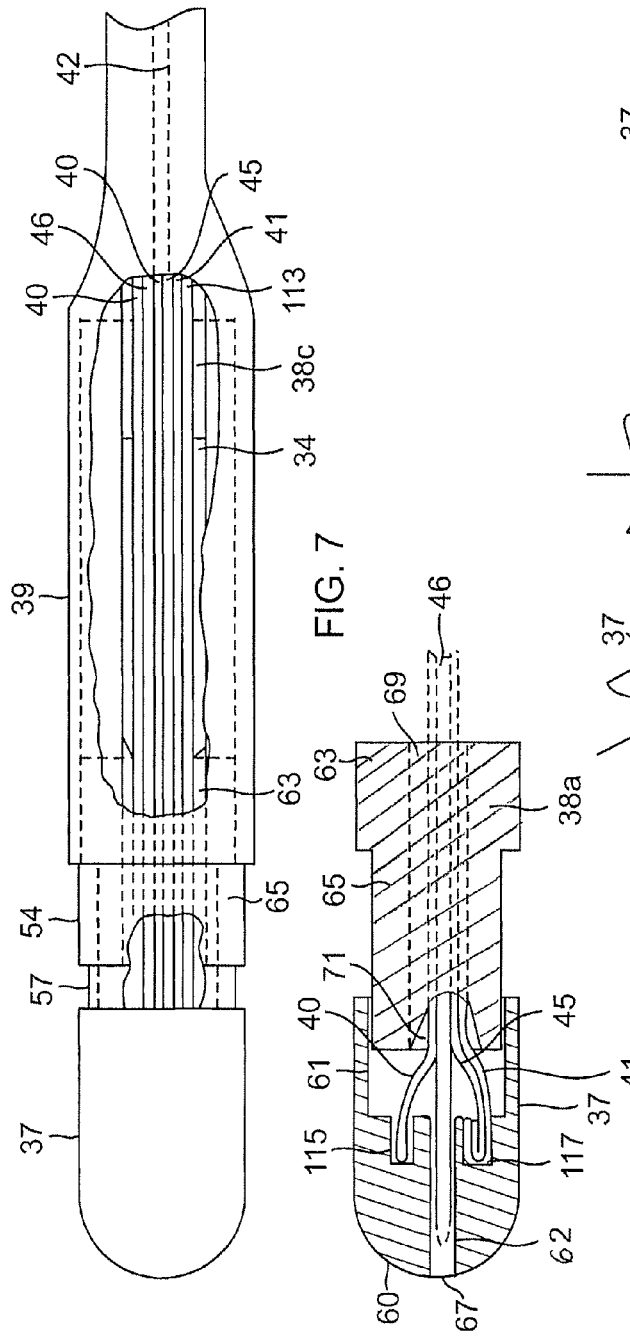
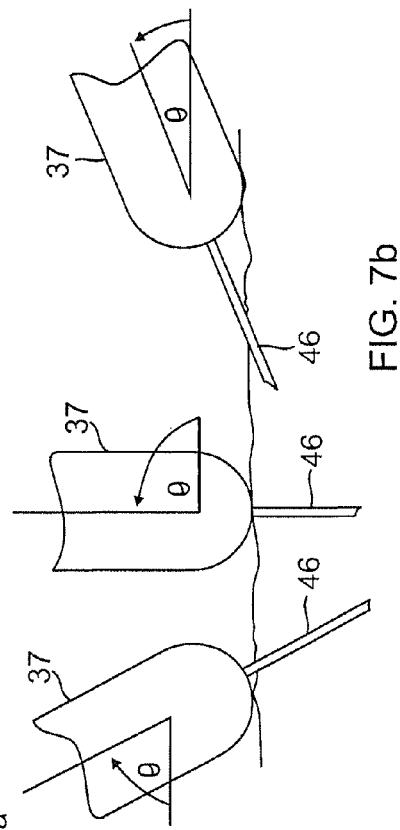
FIG. 7
FIG. 7a
FIG. 7b

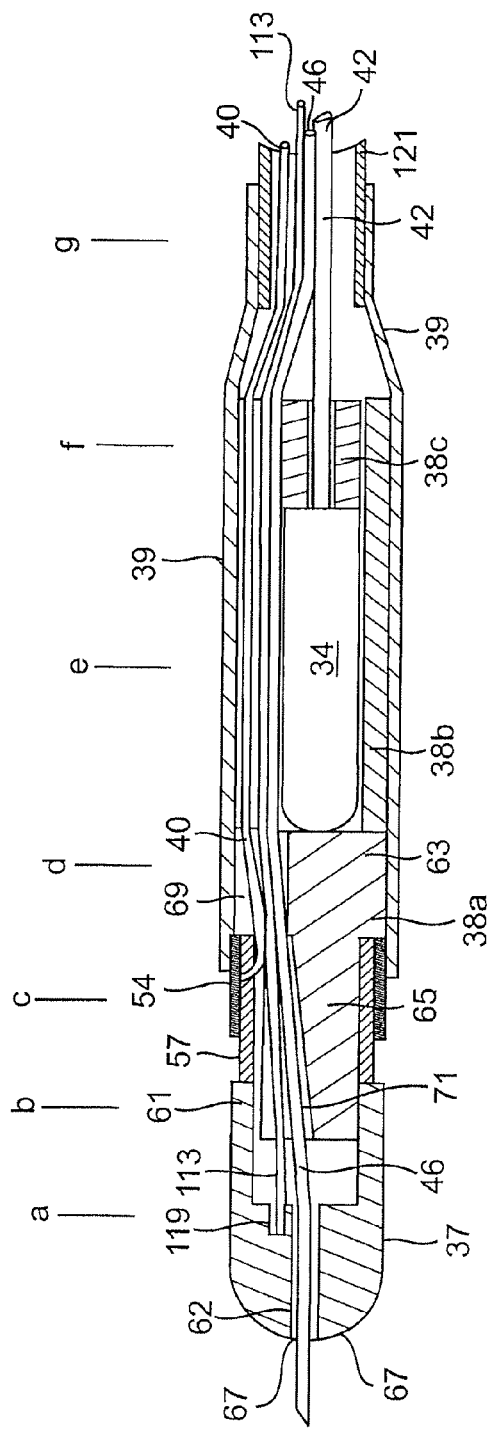
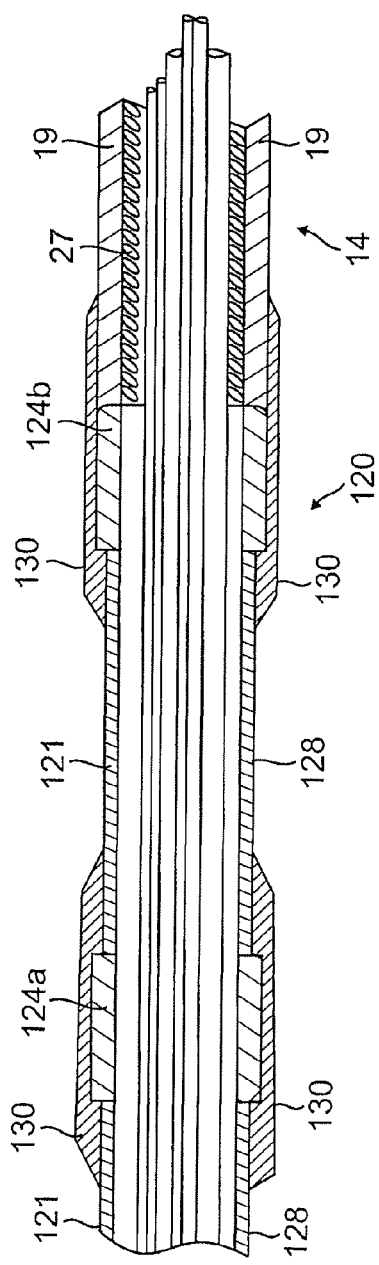
FIG. 8
FIG. 9

MAGNETICALLY GUIDED CATHETER WITH CONCENTRIC NEEDLE PORT

CROSS-REFERENCE TO RELATED APPLICATION(S)

This application is a continuation of and claims priority to and the benefit of U.S. patent application Ser. No. 13/846,904 filed Mar. 18, 2013, now U.S. Pat. No. 9,017,283, which is a divisional of and claims priority to and the benefit of U.S. patent application Ser. No. 12/125,903 filed May 22, 2008, now U.S. Pat. No. 8,480,653, which claims the priority of U.S. Provisional Patent Application No. 60/939,649, filed May 23, 2007, the entire contents of all of which are incorporated herein by reference.

FIELD OF INVENTION

The present invention relates to electrophysiology catheters, and in particular to remote magnetic and injection catheters.

BACKGROUND

Electrode catheters have been in common use in medical practice for many years. They have been used to stimulate and map electrical activity in the heart and to ablate sites of aberrant electrical activity. More recently, therapeutic and diagnostic agents have been delivered into the heart, including the heart wall, through a percutaneous transluminal approach with the use of catheters. In particular, catheters with a needle have been used for injection directly into the myocardium for a variety of treatments, including myocardial revascularization. For example, U.S. Pat. No. 6,309,370 entitled Intracardiac Drug Delivery, the entire disclosure of which is hereby incorporated by reference, is directed methods and apparatuses to provide accurate minimally-invasive methods and apparatus for intracardiac administration of drugs to the myocardium.

In use, the electrode catheter is inserted into a major vein or artery, e.g., femoral. artery, and then guided into the chamber of the heart of concern. Navigation of the catheter has been accomplished largely with the use of fluoroscopy which poses radiation concerns for both the patient and the treating physician. Moreover, within the heart, the ability to control the exact position and orientation of the catheter tip is critical and largely determines how useful the catheter is. Electromagnetic position sensors have been in use in catheter tips for many years. While these sensors provide useful data to determine location and position of the catheter, they can be relatively large and consequently tend to occupy a significant amount of space in the catheter tip.

In recent years, magnetically navigable and controllable catheters have been used. These catheters have allowed more aspects of ablation and mapping procedures to be automated for improved accuracy and efficiency. They also provide the benefit of lowering radiation exposure at least for the treating physicians by enabling catheter control from a remote location away from the patient. However, because space in the catheter tip is at a premium, the integration of ablation, mapping and injection capabilities with magnetic navigation in a catheter tip has been challenging. While such catheters exist, the catheter tips tend to lack sufficient volume of magnetic material for adequate magnetic navigation and control and their needle ports have been generally eccentric or off-axis. Moreover, the injection needle is generally made of a relatively stiff material that allows the translation of force to enable the extension. However, added stiffness tends to make it more difficult to adequately deflect the catheter without increasing magnetic volume. The action of injection requires the tip of the catheter to remain in contact with tissue surface. Insufficient magnetic "adhesion" force would limit the ability of the needle to penetrate tissue.

Accordingly, it is desirable to provide a magnetically navigable and controllable catheter whose tip section carries adequate elements for ablation, mapping and injection. Particularly desirable is a catheter having a tip section with an omnidirectional tip electrode and a concentric needle port for greater tip angulation while housing a position sensor and a sufficient volume of magnetic or magnetizable material to enable suitable magnetic response to an external magnetic surgery system.

SUMMARY OF THE INVENTION

The present invention is directed to an electrophysiology catheter that is adapted for ablation, mapping, injection, and directional control by an external magnetic system, including a magnetic surgery system (MSS). In one embodiment, the catheter has a catheter body, an intermediate section, and a tip section having a tip electrode configured with an omnidirectional distal end and a concentric needle port. The omnidirectional distal end of the tip electrode improves maneuverability and angulation. A dome configuration enables a wide range of tissue contact angles. The concentric needle port provides optimal tissue injection success.

In a more detailed embodiment, the tip electrode houses a magnetic device and a position sensor arranged in an integrated configuration, wherein the configuration facilitates a path in the tip section for a component, including an injection needle, to extend through the tip section for extension and retraction with reduced stress and friction. The integrated configuration is an efficient use of space in the tip electrode that allows the tip section to carry both the position sensor for determining location and orientation of the tip section and the necessary volume of magnetic or magnetizable material for magnetic navigation. The path defined by the integrated magnetic device and position sensor through the tip section can be generally linear or nonlinear depending on the structure design of the magnetic device and position sensor. For the injection needle, the path connects with the concentric needle port whether the path is on axis or off axis with the tip electrode. The catheter also includes a very soft and flexible intermediate section and an even softer and more flexible distal transitional section carrying additional magnetic members to facilitate remote magnetic navigation.

The present invention contemplates the magnetic device having either a monolithic structure or a modular structure comprising multiple pieces. For an integrated arrangement, one or both of the magnetic device and the position sensor are hollow so that they can assume a surrounding relationship, including a circumferential relationship, to minimize the space they occupy in the tip electrode without blocking components from reaching the tip electrode. Moreover, a member of the magnetic device can be configured as a spacer to situate the sensor a predetermined distance from the distal end of the tip electrode so that systems and devices processing signals from the sensors based on a known distance between the sensor and the distal tip of the tip electrode can reliably detect the position of the sensor.

In accordance with a feature of the present invention, the intermediate section or at least a portion thereof is especially floppy and soft for a "soft touch." To that end, the intermediate section is constructed of a low durometer tubing reinforced with a spring coil so that stiffness of the intermediate section stems primarily from the components passing therethrough, including the injection needle and its overtubing. A softer and more flexible distal transitional section carrying additional magnets has no structures beyond connective tubings, the magnetics secured therebetween, and heat shrinking protective sleeves for the magnets, such that stiffness stems primarily from the components extending therethrough.

In more detailed embodiments, the catheter carries a ring electrode for bipolar electrode configuration on the tip section. While the catheter in an embodiment includes a needle injection control handle, the extension and retraction and even actuation of fluid flow through the needle can be automated such as by means of an automated injection device and system such as disclosed in U.S. Patent Application Entitled AUTOMATED INJECTION CATHETER DEVICE AND SYSTEM, naming inventors Christopher J. Birchard, et al., application Ser. No. 12/125,893, now U.S. Pat. No. 8,603,046, the entire disclosure of which is hereby incorporated by reference.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 6A is a longitudinal cross-sectional view of another embodiment of a tip electrode.

FIG. 7 is a top plan view of the tip section of FIG. 5.

FIG. 7a is a cross-sectional view of the tip electrode and distal magnetic member of FIG. 5, taken along a first diameter.

FIG. 7b is a cross-sectional view of the tip electrode at different angles of tissue contact.

FIG. 8 is a cross sectional view of the tip section of FIG. 5, taken along a second diameter.

FIG. 8a is a longitudinal cross sectional view of the tip section of FIG. 8, taken along line a-a.

FIG. 8b is a longitudinal cross sectional view of the tip section of FIG. 8, taken along line b-b.

FIG. 8c is a longitudinal cross sectional view of the tip section of FIG. 8, taken along line c-c.

FIG. 8d is a longitudinal cross sectional view of the tip section of FIG. 8, taken along line d-d.

FIG. 8e is a longitudinal cross sectional view of the tip section of FIG. 8, taken along line e-e.

FIG. 8f is a longitudinal cross sectional view of the tip section of FIG. 8, taken along line f-f.

FIG. 8g is a longitudinal cross sectional view of the tip section of FIG. 8, taken along line g-g.

FIG. 9 is a cross sectional view of an embodiment of a catheter, including a junction between a distal transitional section and the intermediate section.

FIG. 11a is a perspective view of another embodiment of the magnetic device.

DETAILED DESCRIPTION OF THE INVENTION

Figure 1:
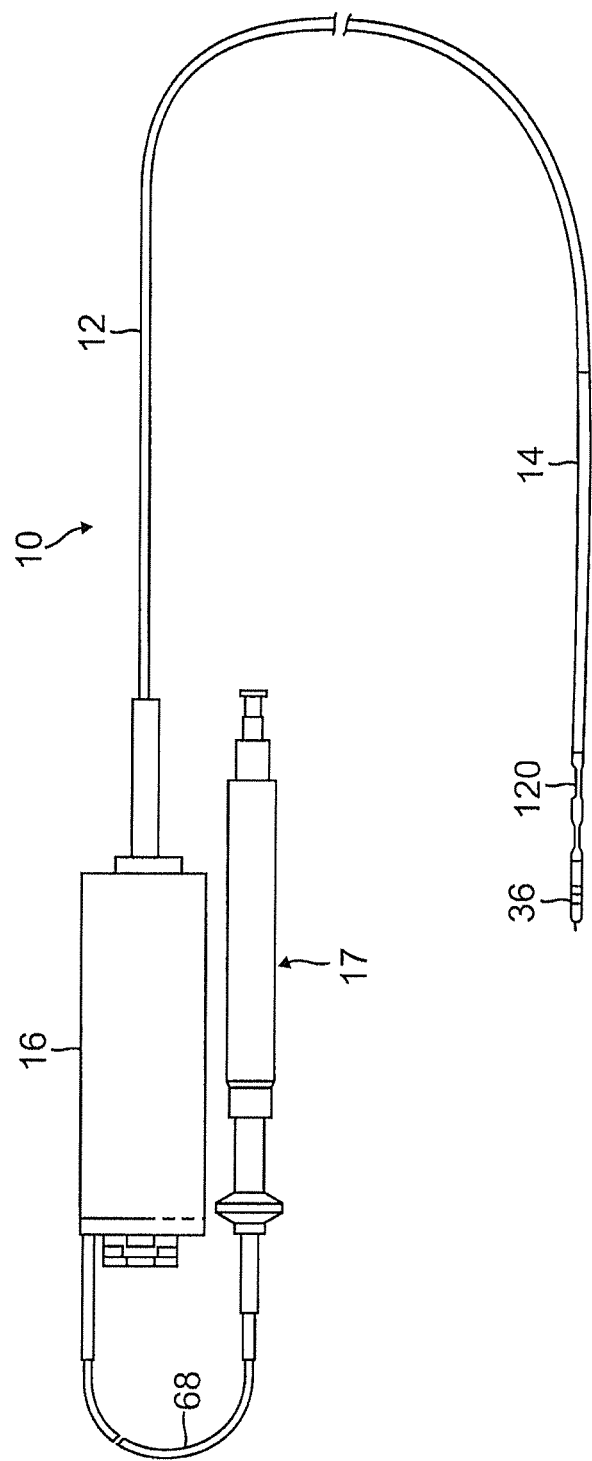
FIG. 1 is a side view of an embodiment of the catheter of the present invention.

As shown in FIGS. 1-9, catheter 10 of the present invention comprises an elongated catheter body 12 having proximal and distal ends, a very soft and flexible intermediate section 14 at the distal end of the catheter body 12, a magnetically-maneuverable tip section 36 through which an injection needle 46 can be extended and retracted, a connection housing 16 at the proximal end of the catheter body and a needle control handle 17 proximal of the housing 16, by which a user can manipulate needle extension and retraction. In accordance with a feature of the invention, the tip section includes a tip electrode 37 for ablation and mapping, an electromagnetic position sensor 34 to provide location and orientation data, and a magnetic device 38 to facilitate magnetic navigation and control.

Figure 2:
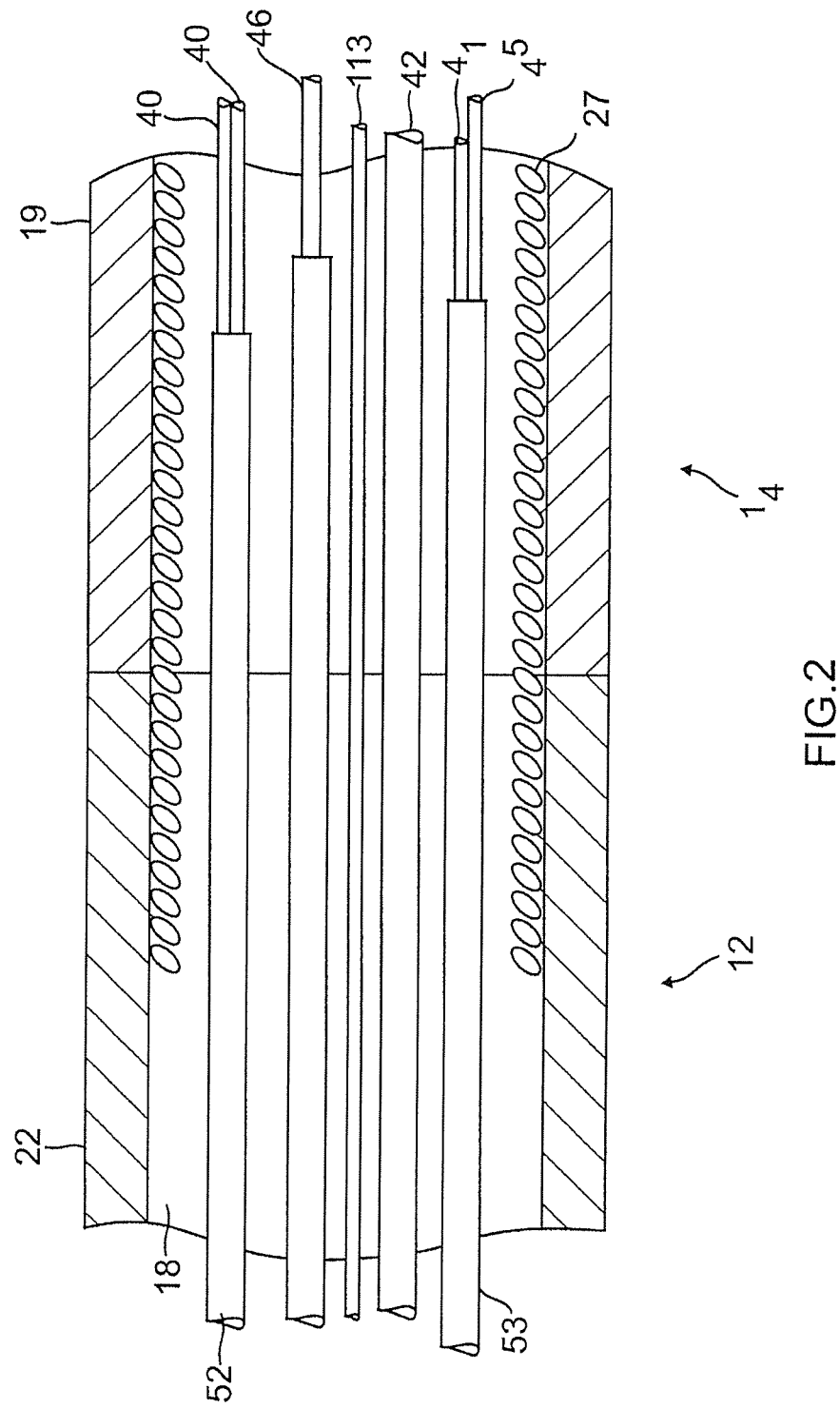
FIG. 2 is a side cross-sectional view of an embodiment of a catheter according to the invention, including a junction between a catheter body and an intermediate section.

With reference to FIGS. 1 and 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that the catheter body 12, the intermediate section 14 and the tip section 36 of the catheter 10 all rotate in a corresponding manner.

Extending through the single lumen 18 of the catheter body 12 are components, for example, an injection needle 46, lead wires 40 to energize electrodes and thermocouple wires 41 to sense tip and/or tissue temperature. A single lumen catheter body can be preferred over a multi-lumen body because it has been found that the single lumen body permits better tip control when rotating the catheter. The single lumen permits the aforementioned components to float freely within the catheter body and minimize undesirable performance characteristics such as unintended rotation, twisting or flipping of the catheter body.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The braided outer wall 22 provides improved torsional stability while at the same time minimizing the wall thickness of the catheter, thus maximizing the diameter of the central lumen 18. The catheter body 12 may have an outer wall 22 with an outer diameter of from about 0.090 inch to about 0.104 inch and an inner diameter of from about 0.061 inch to about 0.075 inch. In one embodiment, the catheter body 12 is constructed of braided PEBAX tubing.

Referring also to FIG. 2, the intermediate section 14 distal of the catheter body 12 comprises a shorter section of tubing 19 having a single lumen. The tubing 19 is made of a suitable non-toxic material that is considerably softer and more flexible than the catheter body 12. A suitable material for the tubing 19 is PEBAX tubing with a low to medium durometer plastic, for example, within the ranges of about 25 D to 55 D, preferably of about 30 D to 40 D, more preferably of about 35 D. The outer diameter of the intermediate section 14, like that of the catheter body 12, is preferably no greater than about 8 french, more preferably less than 7 french. (0.092 inch). The length of the tubing 19 is within the ranges of about 1.5 in. to 8.0 in., preferably of about 2.0 in. to 6.0 in., more preferably of about 4.0 in to 5.0 in. Notably, stiffness of the intermediate section 14 is provided primarily by the components extending through it such as the lead wires, safety wire, electromagnetic position sensor cable, and injection needle, although there is a spring coil 27 extending within the tubing 19. It is a feature of the present invention that the intermediate section has a "soft touch" in that it is sufficiently soft, and flexible and allows the tip section to be adequately maneuvered by the MSS notwithstanding the presence of the aforementioned components, including a nitinol injection needle and its overtubing.

The catheter body 12 may be attached to the intermediate section 14 by butt fusing the distal end of the tubing of the catheter body and the proximal end of the tubing 12 using a combination of heat, pressure (along the longitudinal axis). A PET shrink sleeving is used temporarily to control the flow of the PEBAX and removed after the ends have fused. The spring coil 27 extends proximally into the catheter body 12 a short distance (for example, about 3.0 mm) to ensure adequate anchorage.

Figure 3:
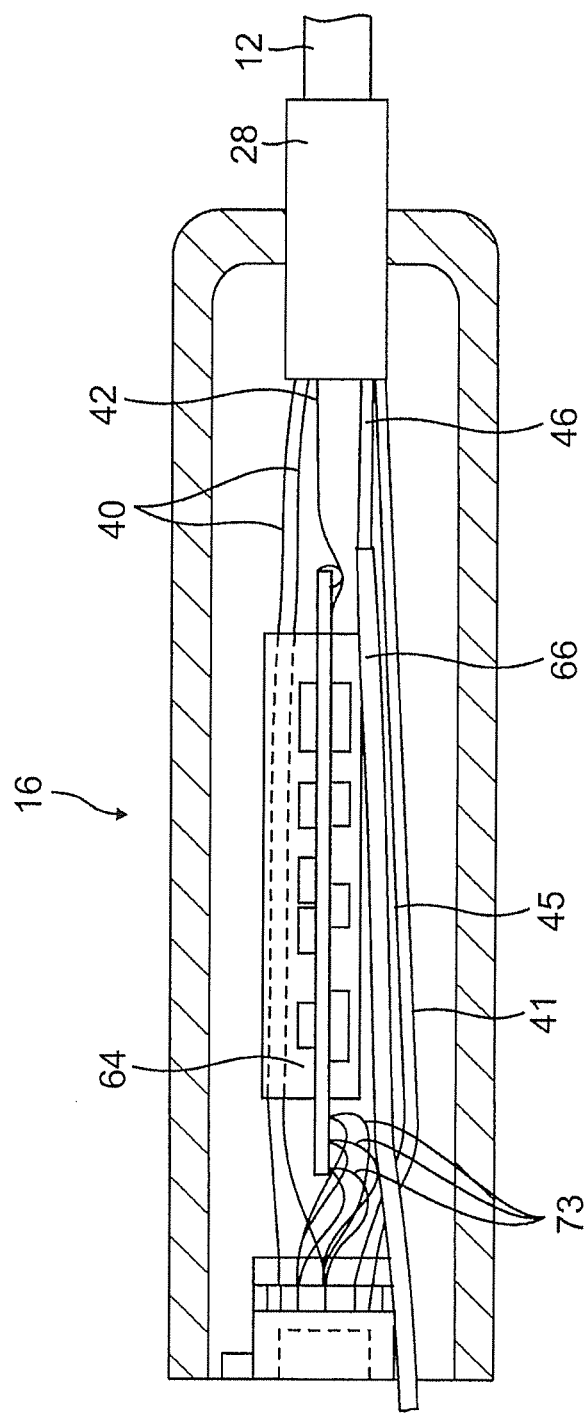
FIG. 3 is a side cross-sectional view of an embodiment of a connection housing according to the invention.

With reference to FIG. 3, distal of the catheter body 12 is the connection housing 16 for various components, including the lead wires 40, thermocouple wires 41 and 45, the injection needle 46 and electromagnetic sensor cable 42, all of which extend into the housing through the catheter body by means of a shrink sleeve 28. The lead wires 40 extend out through housing 16, and terminate at their proximal end in an input jack (not shown) that may be plugged into an appropriate signal processing unit (not shown) and source of RF energy (not shown). The electromagnetic sensor cable 42 connects to a circuit board 64 in the housing 16. The circuit board 64 amplifies the signal received from the electromagnetic sensor 34 and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor 34, from being used twice. The connection housing 16 is illustrated as a generally cylindrical structure, but it is understood by one of ordinary skill in the art that the housing may assume any shape or configuration, including that of a conventional catheter control handle, to facilitate its handling, use and or storage by a user.

The wires 41 and 45 extend out through the housing 16 and to a connector (not shown) connectable to a temperature monitor (not shown). The injection needle 46 and protective tube 47 extend through one or more guide tube 66, preferably made of polyurethane, and are afforded longitudinal movement and protection against buckling, sharp bends in the housing and contact with the circuit board, as they emerge from the proximal end of the housing toward the needle control handle 17.

Figure 4:
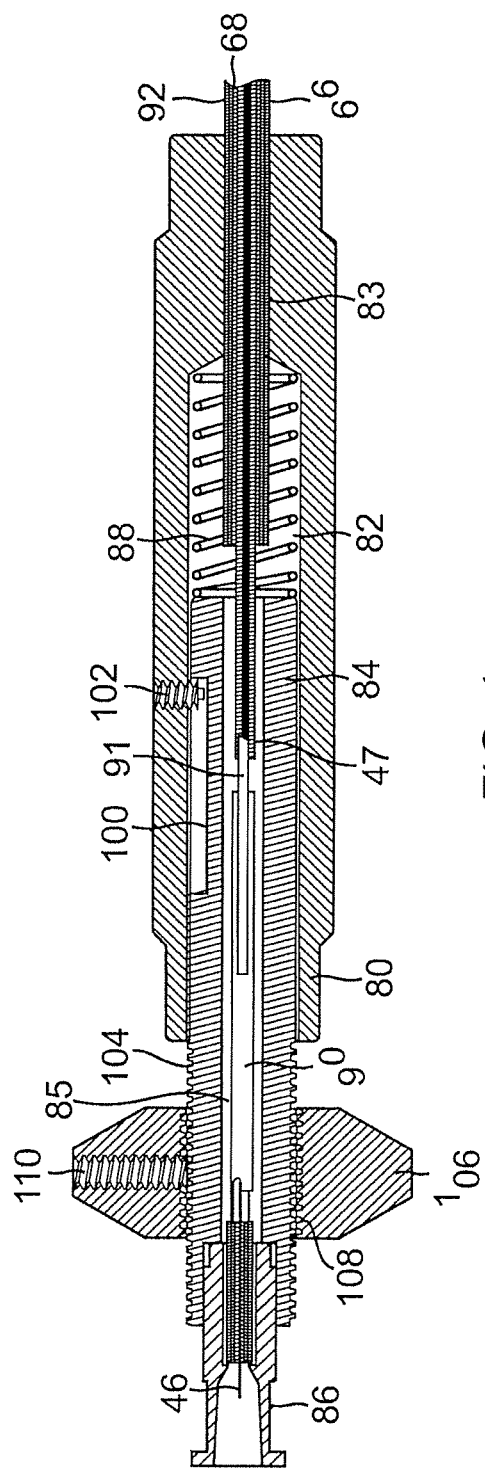
FIG. 4 is a side cross-sectional view of an embodiment of a needle control handle according to the invention, in a resting configuration where the injection needle is in the retracted position.
Figure 4A:
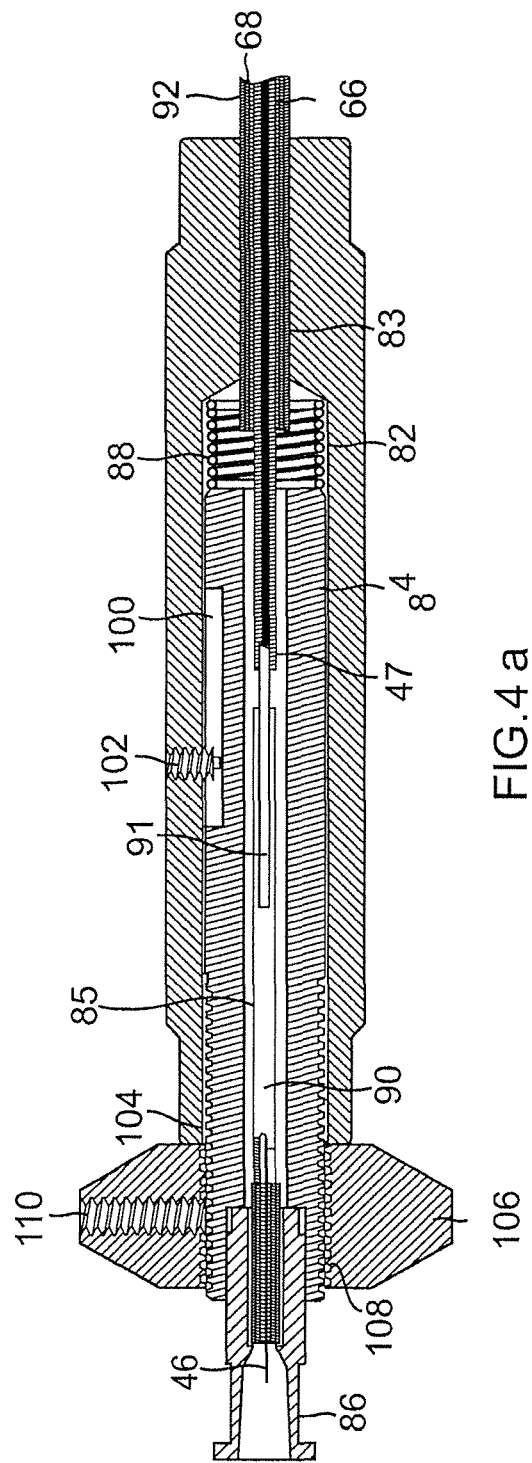
FIG. 4a is a side cross-sectional view of an embodiment of a needle control handle according to the invention, in an actuated configuration where the injection needle is in the extended position.

Extension and retraction of the injection needle 46 in the tip electrode 37 is accomplished by the needle control handle 17. In the illustrated embodiment of FIGS. 4 and 4*a*, the needle control handle 17 comprises a generally cylindrical outer body 80 having proximal and distal ends, a piston chamber 82 extending a part of the way therethrough, and a needle passage 83 extending a part of the way therethrough. The piston chamber 82 extends from the proximal end of the handle part way into the body 80, but does not extend out the distal end of the body. The needle passage 83, which has a diameter less than that of the piston chamber 82, extends from the proximal end of the piston chamber to the proximal end of the outer body 80.

A piston 84, having proximal and distal ends, is slidably mounted within the piston chamber 82. A luer connector 86 is mounted in the proximal end of the outer body. The piston 84 has an axial passage 85 through which the injection needle 46 extends, as described in more detail below. A compression spring 88 is mounted within the piston chamber 82 between the distal end of the piston 84 and the outer body 80.

The proximal end of the injection needle 46 is mounted to the luer connector 86 by means of a first rigid tube 90, preferably made of stainless steel, which has a proximal end fitted into the luer connector. This arrangement fixedly attaches the injection needle 46 to the piston 84 so that it moves longitudinally with the piston. The first rigid tube 90 is also fixedly attached to the piston 84 and moves longitudinally with the piston. The injection needle 46 and first rigid tube 90 extend through the axial passage 85 of the piston 84. Within the axial passage 85, a second rigid tube 91, preferably made of stainless steel, has a proximal end mounted coaxially within the distal end of the first rigid tube 90. The proximal end of the second rigid tube 91 is mounted within the protective tube 47, which has its proximal end inside the axial passage 85, and the distal end of the second rigid tube is attached, directly or indirectly, to the outer body 80. The guide tube 66, through which the protective tube 47 and injection needle 46 extend, as discussed above, is fixedly attached to the outer body 80 by means of a shrink sleeve 92, as is generally known in the art.

In use, force is applied to the piston 84 to cause distal movement of the piston relative to the body 80, which compresses the compression spring 88. This movement causes the injection needle 46 to correspondingly move distally relative to the body 80, guide tube 66, protective tube 47 and catheter body 12, so that the distal end of the injection needle extends outside the distal end of the tip electrode 37. When the force is removed from the piston, the compression spring 88 pushes the piston 84 proximally to its original position, thus causing the distal end of the injection needle 46 to retract back into the tip electrode 37. Upon distal movement of the piston 84, the first rigid tube 91 moves distally over the second rigid tube 91 to prevent the injection needle 46 from buckling within the axial passage 85.

The piston 84 further comprises a longitudinal slot 100 extending along a portion of its outer edge. A set screw 102 extends through the outer body 80 and into the longitudinal slot 100. This design limits the distance that the piston can be slid proximally out of the piston chamber 82. When the distal end of the injection needle 46 is in the retracted position, the set screw 102 can be set at or near the distal end of the longitudinal slot 100.

The proximal end of the piston 84 has a threaded outer surface 104. A circular thumb control 106 is mounted on the proximal end of the piston. The thumb control 106 has a threaded inner surface 108 that interacts with the threaded outer surface 104 of the piston. The thumb control 106 acts as a stop, limiting the distance that the piston 84 can be pushed into the piston chamber 82, and thus the distance that the injection needle 46 can be extended out the distal end of the catheter. The threaded surfaces of the thumb control 106 and piston 84 allow the thumb control to be moved closer or farther from the proximal end of the outer body 80 so that the extension distance of the injection needle can be controlled by the physician. A tension screw 110 is provided in the thumb control 106 to control the tension between the thumb control and piston 84. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston. Suitable needle control handles are described in U.S. Pat. Nos. 6,540,725 and 6,575,931, and U.S. application Ser. No. 12/125,890, now U.S. Pat. No. 8,192,399, the entire disclosure of which is hereby incorporated by reference.

Figure 5:
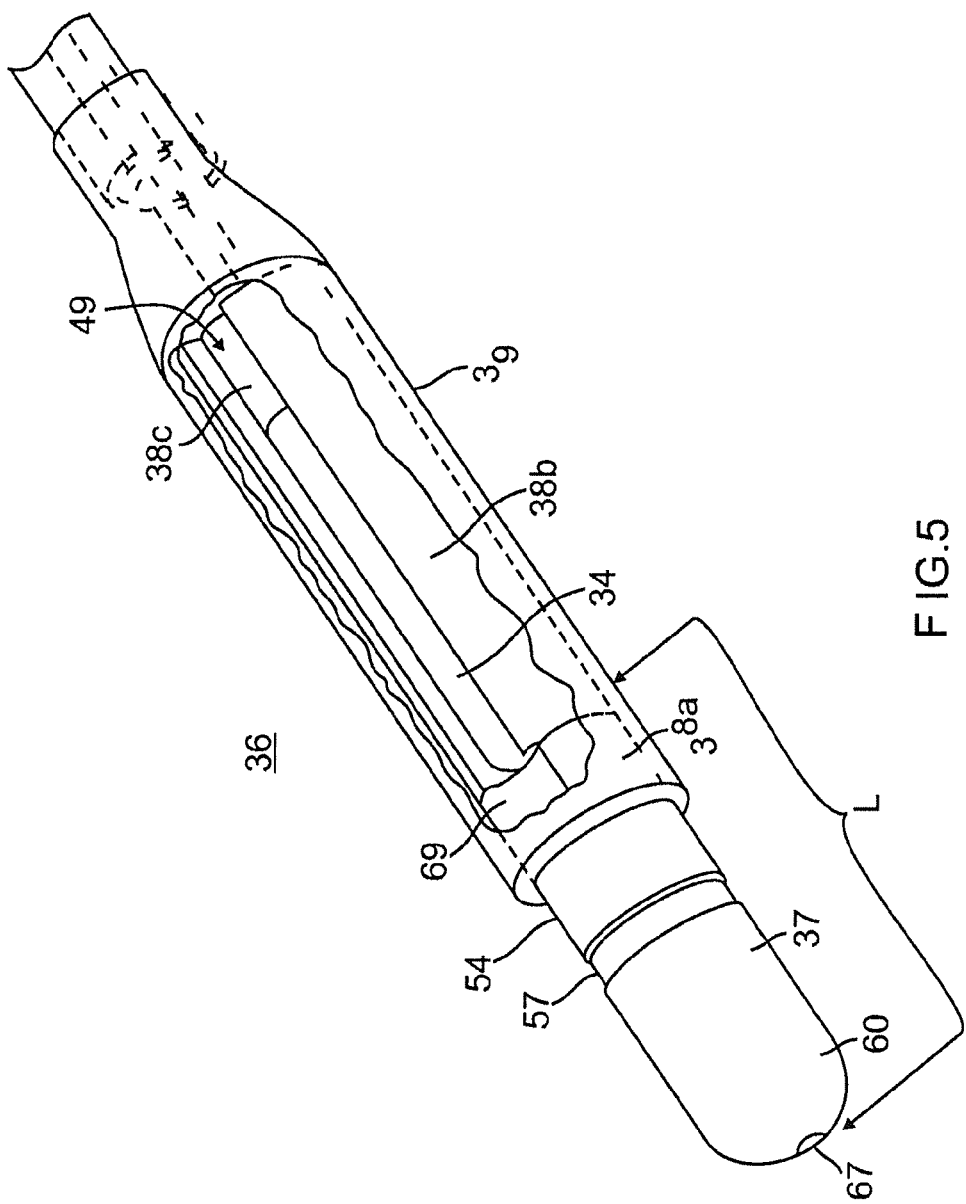
FIG. 5 is a perspective view of an embodiment of a tip section according to the invention.

Distal end of the intermediate section 14 is the tip section 36 that includes the tip electrode 37 adapted for ablation and needle injection, an embodiment of which is illustrated in FIG. 5. Also provided is a ring electrode 54 proximal of the tip electrode and separated therefrom by a short segment of insulating tubing 57. Included in the tip section 36 are the electromagnetic position sensor 34 and the magnetic device 38 housed together in a heat shrink protective tubing 39 (shown partially broken away) extending between the ring electrode and the proximal end of the tip section.

As understood by one of ordinary skill in the art, the electromagnetic position sensor 34 enables determination of position and orientation coordinates (for example, x, y, z, pitch, roll, yaw) of the tip section. Suitable electromagnetic sensors for use in connection with the present invention are described, for example, in U.S. Pat. Nos. 4,391,199 and 6,201,387, the disclosures of which are hereby incorporated by reference. A suitable electromagnetic mapping sensor is manufactured by Biosense Webster, Inc. and marketed under the trade designation NOGA. A suitable system for monitoring and displaying the signals received from the electrodes and electromagnetic sensor is marketed under the trade designation Biosense-NOGA system. The sensor 34 is connected to the proximal end of sensor cable 42. The electromagnetic sensor cable 42 comprises multiple wires encased within a plastic sheath.

To use the electromagnetic sensor, the patient is placed in a magnetic field generated, for example, by situating under the patient a pad containing coils for generating a magnetic field. A reference electromagnetic sensor (not shown) is fixed relative to the patient, e.g., taped to the patient's back, and the catheter 10 containing the electromagnetic sensor 34 is advanced into the patient's heart. Each sensor comprises three small coils which in the magnetic field generate weak electrical signals indicative of their position in the magnetic field. Signals generated by both the fixed reference sensor and the sensor 34 in the heart are amplified and transmitted to a computer which analyzes the signals and then displays the signals on a monitor. By this method, the precise location and orientation of the sensor 34 in the catheter relative to the reference sensor can be ascertained and visually displayed. The sensor 34 can also detect displacement of the catheter that is caused by contraction of the heart muscle.

The magnetic device 38 in the tip section 36 responds to a magnetic surgery system (MSS) (not shown) that applies magnetic fields and gradients from outside the patient body so as to manipulate and direct the tip section. For optimum response to the MSS, the magnetic device (whether as monolithic piece or as a modular combination of multiple pieces) occupies a predetermined volume within the tip section so that the MSS can have suitable magnetic control over the tip section for deflection and positioning against the heart wall. The ability of the MSS to hold the tip section in position is of particular importance during injection. Successful penetration of the needle into the heart wall requires the tip electrode to be held securely against the heart wall.

A suitable magnetic material for construction of the magnetic device 38 is a Neodymium Iron Boron (NdFeB) magnet, a commercialized permanent magnet material. NdFeB magnets are available in a number of different grades that span a wide range of properties and application requirements. NdFeB magnets are available in sintered as well as bonded forms. NdFeB magnets can be brittle and machining operations should be performed prior to magnetization, using diamond tools. NdFeB magnets are manufactured in the following forms: sintered, compression bonded, injection molded and extruded. Suitable NdFeB magnets are manufactured by Magnetic Sales & Manufacturing Inc. and marketed under the trade designation TOTAL MAGNETIC SOLUTIONS. Although it is understood by one of ordinary skill in the art that the tip section can employ any suitable magnetic or magnetizable material, a monolithic or solid design of the magnetic device 38 can allow for faster assembly of the tip section; however, a modular design can ease manufacturing and handling requirements.

In accordance with a feature of the present invention, the tip electrode 37 has an atraumatic omnidirectional domed outer surface 60 at its distal end. With reference to FIGS. 5, 7a and 8, a distal portion of the tip electrode has an axially-aligned duct 62 which at its distal end defines an injection needle port 67 that is advantageously concentric with the distal end of the tip electrode 37. The domed distal design and the concentric port allow for maximum contact with between the distal end and endocardial tissue 100 and for maximum penetration of the needle 46 into myocardium tissue 102 for all intended angles θ of contact with normal healthy heart wall ranging between about 10 to 90 degrees, preferably ranging between about 20 to 90 degrees, and more preferably ranging between about 45 to 90 degrees, as shown in FIG. 7b. A proximal end 61 of the tip electrode 37 is trepanned so as to receive a distal end of the magnet device 38, as described below in further detail.

Figure 6:
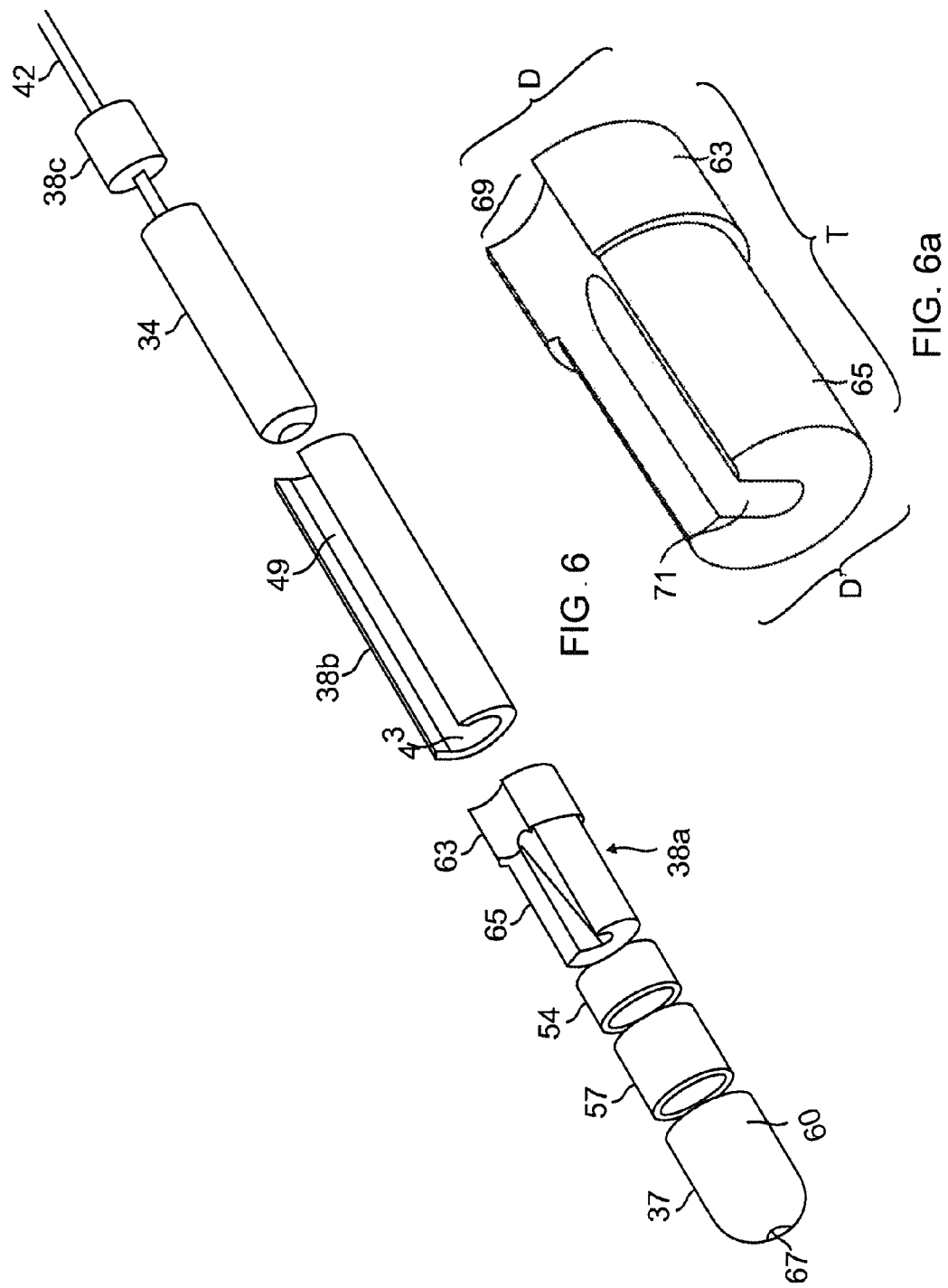
FIG. 6 is an exploded view of the tip section of FIG. 5.
Figure 10:
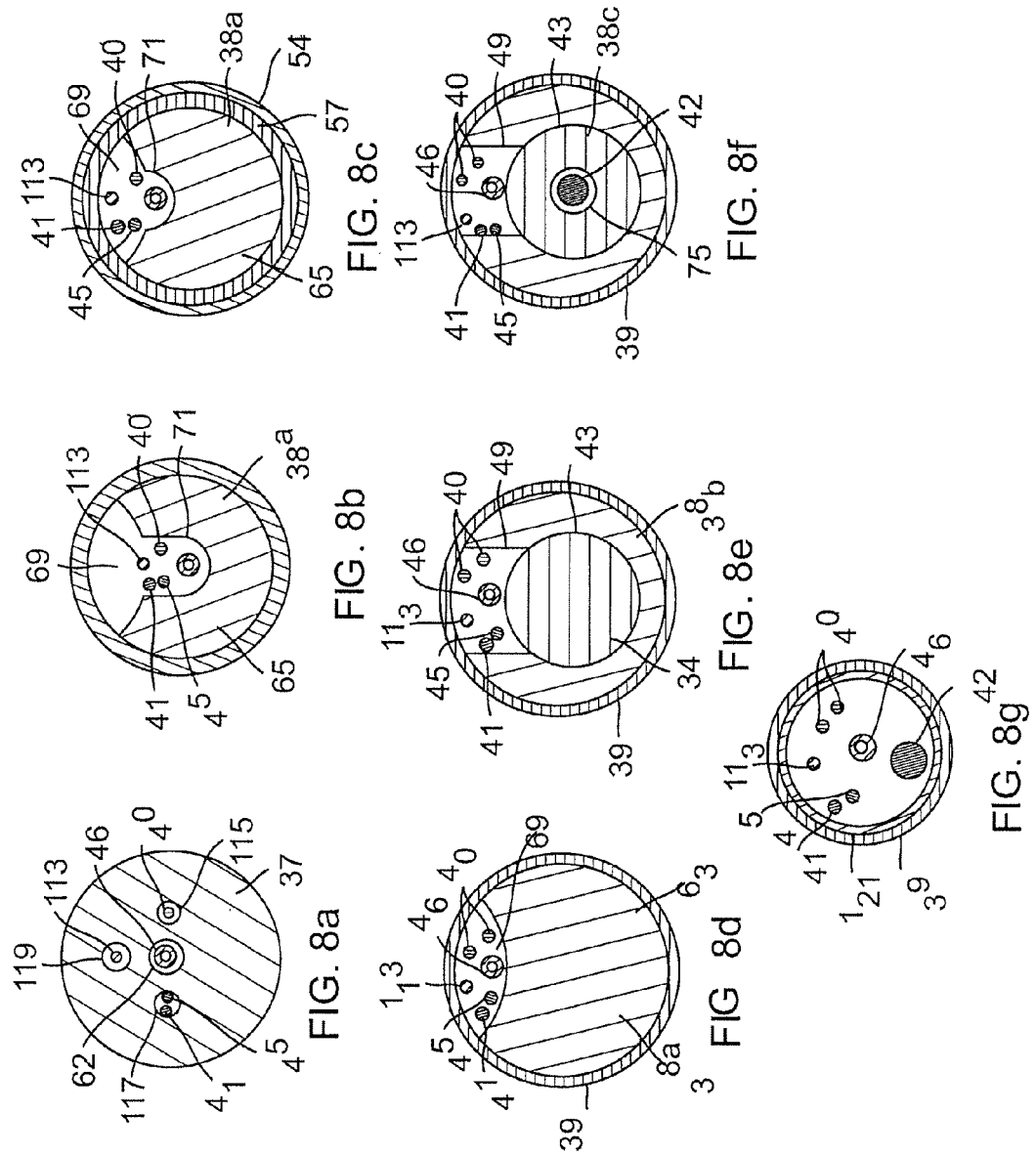
FIG. 10 is a perspective view of another embodiment of a tip section according to the invention.

In the illustrated embodiment of FIGS. 5 and 6, the position sensor 34 has a generally solid elongated cylindrical configuration and is integrated with a modular magnetic device 38 which includes a distal magnetic member 38a, a mid-member 38b and a proximal magnetic member 38c that surrounds the sensor 34 for efficient use of space within the tip section 36. Each of the magnetic members has an overall generally cylindrical configuration, and when assembled, the modular magnetic device 38 defines a path for components to circumvent the position sensor 34 and extend between the tip electrode 37 and the intermediate section 14.

The mid-member 38b has a C-shaped cross section with an outer diameter D, a cylindrical cavity 43 and an outer channel 49. The diameter and length of the cylindrical cavity 43 are sized so that the cavity can house the sensor 34 and the proximal magnetic member 38c.

The distal member 38a has a proximal portion 63 and a neck portion 65 (see FIG. 6a). The proximal portion has an outer diameter D comparable and generally equal to the outer diameter D of the mid-member 38b. In the illustrated embodiment, the neck portion 65 has a smaller diameter D' that allows the neck 65 to be inserted into the trepanned proximal end 61 of the tip electrode. The distal member 38a is also configured along its length with a notched portion 69 such that both the proximal portion 63 and the neck portion 65 have a crescent-shaped cross section (see FIGS. 8b, 8c and 8d). There is also a channel 71 inclined from the upper edge along the length of the distal member 38a (see FIG. 6a). The channel 71 at the distal end is deeper than the notched portion 69 (see FIG. 8b). The channel 71 at the proximal end is nearly even with the notched portion 69 such that the channel has diminished (FIG. 8d).

As illustrated in FIGS. 5 and 6, the sensor 34 is integrated in the cavity 43 of the mid-member 38b, and is sandwiched between the proximal member 38c and the distal member 38a. The proximal member 38c has an inner passage 75 for the sensor cable 42 to pass through. As illustrated in FIG. 5, the distal member 38a is in general contact with distal ends of the mid-member 38b and the sensor 34, with its inclined channel 71 and notched portion 69 longitudinally aligned with the outer channel 49 of the mid-member 38b.

The insulating tubing 57 and the ring electrode 54 are slid over the neck portion 65 before the neck portion is inserted into the trepanned proximal end 61 of the tip electrode 37. As shown in FIG. 6, the sensor 34 and the magnetic device 38 form an integrated, generally cylindrical configuration with the sensor 34 and the mid-member 38b in a surrounding, circumferential and coaxial relationship. Advantageously, the sensor 34 is housed in its entirety in the magnetic device 38 for efficient use of space in the tip section 36. Moreover, this integrated design provides a continuous and unobstructed path 111 for components such as the lead wires 40, the injection needle 46, thermocouple wires 41 and 45 and a tip electrode safety wire 113 to extend alongside the position sensor 34 and the magnetic device 38 throughout the tip section 36. Depending on the component, the path 111 includes the duct 62 in the tip electrode 37, the inclined channel 71 of the distal magnetic member 38a, and the outer channel 49 of the mid-member 38b. In the illustrated embodiment, the injection needle travels the entirety of path 111 in the tip section. In accordance with a feature of the present invention, the tip section 36 allows for the integration of the generally solid position sensor 34 and the magnetic device 38 while providing a concentric needle port 67.

In the illustrated embodiment, about half of the length of the tip electrode 37 is trepanned to receive the neck 65 of the distal magnetic member 38a. Notably, a length T of the distal magnetic member 38a (FIG. 6a) is predetermined, along with the length of the tip electrode 37, so that the distal end of the sensor 34 is positioned a predetermined distance L (FIG. 5) from the distal end of the tip electrode 37. Systems and programs that process the position and orientation signals from position sensors typically operate with a known distance L such that any deviation in the actual distance between the distal end of the tip electrode and the distal end of the sensor to the distance L can cause a misreading of the position and/or orientation. Thus, in instances where the distance L is relevant, care is given to the proper assembly of the members 38a, 38b and 38c and the sensor 34 such that the distal ends of the mid-member 38b and the sensor 34 abut the proximal end of the distal member 38a. Moreover, the total volume of the magnetic devices as provided by the members 38a, 38b and 38c satisfies the predetermined volume required for the tip section 36 to be maneuvered by the MSS for suitable deflection and positioning against the heart wall.

The injection needle 46 extends from the needle control handle 17, through the connection housing 16, the catheter body 12, the intermediate section 14 and the tip section 36. As illustrated in FIG. 3, the injection needle 46 can be formed with a beveled or unbeveled edge at the distal tip of the needle. The needle 46 is coaxially mounted within a protective tube 47, preferably made of polyimide, which serves to prevent the needle from buckling and also serves to electrically insulate the needle from the tip electrode 37. The protective tube 47 additionally serves to provide a fluid-tight seal surrounding the injection needle 46. FIG. 8 depicts the injection needle 46 extending beyond the distal end of the tip electrode 37, as it would be positioned in order to infuse diagnostic or therapeutic fluid into the myocardium. As shown in FIG. 7a, the distal end of the injection needle 46 is withdrawn into the tip electrode 37 during the period of time that the catheter is inserted through the vasculature of the body and also during the period of time in which the catheter is removed from the body to avoid injury. The injection needle 46 is extendable beyond the distal end of the catheter and retractable therefrom. If desired, the catheter can include a needle stop mechanism for limiting the distance that the needle extends beyond the distal end of the tip section 36. Such a mechanism is described in U.S. Pat. No. 6,623,474, the entire disclosure of which is hereby incorporated by reference.

While the injection needle 46 can be made from one or more straight pieces of small diameter tubing having an outer diameter that allows the tubing to fit within the catheter, the injection needle of the illustrated embodiment is a single piece of nitinol tubing. In one embodiment, the injection needle 46 has an inner diameter ranging from about 0.007 inch to about 0.011 inch, and an outer diameter ranging from about 0.012 inch to about 0.016 inch. In one embodiment, the injection needle 46 has a total length ranging from about 65 to about 85 inches, more preferably about 75 inches.

The tubing of the needle 46, whether plastic or metal, preferably is flexible and has straight position memory so that when it is bent temporarily, its natural tendency is to spring back to the straight position. These properties are particularly desirable in the distal region of the injection needle (i.e., the portion of the needle within the intermediate section 14) so that the needle bends and accommodates the deflection of the intermediate section but returns to its straight position afterwards and pushes the intermediate section 14 back toward the straight position to the same axis as the catheter body 12.

Additionally, the tubing of the needle 46 can be made of a biocompatible material that is capable of being beveled. The material for the tubing preferably also has a low coefficient of friction, a good surface finish for slidability within the catheter, and the ability to be cleaned and sterilized. The good surface finish also reduces coagulate build-up on the needle. The tubing may also have the ability to bond or fuse to an adapter for infusion.

Another suitable plastic for construction of the injection needle is PEEK (polyetheretherketone), although other suitable plastics such as polycarbonate, polyimide, fiberglass, and composites thereof could also be used. Suitable metals for use in connection with the present invention include Nitinol and stainless steel, although Nitinol is preferred for use at the distal region of the needle due to its shape-memory properties. If desired, at least the distal portion of the tubing is provided with a lubricious coating, such as Teflon® or silicone, preferably having a thickness ranging from about 0.0003 inch to about 0.002 inch. In another alternative embodiment, a biocompatible lubricant, such as mineral oil is injected around the needle once assembled.

In accordance with a feature of the invention, the injection needle 46 is sufficiently flexible and has sufficient shape memory such that it can be extended and retracted along the path 111 in the tip section 36. The injection needle extends through the lumen of the tubing 19 of the intermediate section 14 and the lumen of the catheter body 12 toward the connection housing 16. Where the tubing 19 of the intermediate section has a smaller diameter than the tip section 36, all components that extend from the outer channel 49 of the mid-member 38b smoothly conform to the change in diameter under the polyester heat shrink tubing 39 to form an atraumatic profile (see FIGS. 8 and 13). The tubing 39 extends from the ring electrode 54 and to a location proximal of the magnetic device.

To connect the tip and ring electrodes for mapping and/or RF ablation separate lead wires 40 extend through the tip section, the intermediate section 14, the catheter body 12, and the connection housing 16, and terminates at its proximal end in an input jack (not shown) or connector 77 that may be plugged to an generator or the like (not shown). Any portion or portions of the lead may be enclosed within protective sheaths (not shown). In the disclosed embodiment, portions of the lead wires in the tip section 36 and immediately distal of and within the housing 16 are enclosed in the sheath 52. The protective sheath 52 can be made of any suitable material, preferably Teflon®.

Any conventional temperature sensing means, e.g., a thermocouple or thermistor, may be used in the catheter in applications where it is desirable to know the tip or tissue temperature, such as during ablation. In the illustrated embodiment, a suitable temperature sensing means for the tip section comprises the thermocouple formed by a wire pair. One wire of the wire pair is the copper wire 41, e.g., a 40 gauge or similar size copper wire. The other wire of the wire pair is the constantan wire 45, which gives support and strength to the wire pair. The wires 41 and 45 extend through the lumen of the tubing 19 in the intermediate section 14. Any portion or portions of the wires 41 and 45 may be enclosed in protective sheaths (not shown). In the disclosed embodiment, portions of the wires 41 and 45 in the tip section 36 and immediately distal of and within the housing 16 are enclosed in the sheath. Alternatively, the temperature sensing means may be a thermistor. A suitable thermistor for use in the present invention is Model No. AB6N2-GC14KA143T/37C sold by Thermometrics (New Jersey).

The safety wire 113 also extends into tip electrode 37 as a safety precaution to prevent the tip electrode from detaching, and in the event of detachment, to tether the tip electrode to the catheter. A distal end of the safety wire is anchored in the tip electrode in blind hole 119 (FIG. 8) and a proximal end is anchored at a location of the catheter shaft proximal of the portion of the catheter that enters the patient's body. The safety wire can be a Monell wire wrapped with copper.

As understood by one of ordinary skill in the art, distal end of the lead wire 40 for the tip electrode 37 is anchored (e.g., by soldering) in a blind hole 115 (FIG. 7a) in a proximal face of the tip electrode. Distal ends of the thermocouple wires 41 and 45 are likewise anchored in a blind hole 117 (FIG. 7a) in the proximal face. The lead wire 40 for the ring electrode is soldered at its distal end to an inner surface of the ring electrode (FIG. 8) through a hole formed in the tubing 57. The solder location is aligned with the inclined channel 71 of the distal magnetic member 38a so that the lead wire 40 join the other components such as the tip electrode lead wire 40, the thermocouple wires 41 and 45, the injection needle 46, the safety wire 113 passing through the outer channel 49 of the mid-member 38b toward the intermediate section 14 (see FIG. 7).

In the illustrated embodiment, a distal transitional section 120 extends between the tip section 36 and the intermediate section 14. As shown in FIGS. 8 and 9, the section 120 comprises short segments 121 of very soft and flexible tubing in between which are positioned additional magnetic devices 124. In the disclosed embodiment, the section 120 is without a stiffening tube, braiding or any other reinforcing structure. As such, the section 120 is floppy and considerably softer and more flexible than the intermediate section 14. The tubing can be PEBAX tubing with durometer ranging between about 25 D and 55 D, preferably about 25 D and 35 D, and more preferably about 25 D. And, as illustrated in FIG. 9, there are two additional magnetic devices 124a and 124b, each being generally cylindrical with an inner passage through which the components can extend. To secure and protect the additional magnet devices, each has a heat shrink magnetic sleeve tubing 130. Like the magnetic device 38, the additional magnets 124 are responsive to the MSS and provided additional control for deflecting and positioning the tip section 36. Components including the lead wires, the thermocouple wires 41 and 45, the safety wire 113, and the electromagnetic sensor cable extend through the hollow interior of the transitional section 120.

The catheter 10 described above provides advantageous features, including a tip section 36 with an integrated position sensor 34 and magnetic device 38 housed at a location optimally near the tip electrode 37. As understood by one of ordinary skill in the art, space is at a premium in a catheter tip section and the tip section of the present invention efficiently integrates the solid position sensor and the modular magnetic device such that the tip section can accommodate the needed predetermined volume of the magnetic device for proper response to the MSS while still carrying the position sensor at a predetermined distance from the distal end of the tip electrode.

FIGS. 10-13 illustrate another embodiment of a magnetically maneuverable tip section 36' for ablation and injection, in accordance with the present invention. The tip section 36' has structures similar to the tip section 36 described above but both a position sensor 34' and a magnetic device 38' have a hollow design to provide a generally linear passage 119 for the components extending through the tip section, such as the injection needle 46, the lead wire 40 for the tip electrode, the safety wire 113, and the thermocouple wires 41 and 45. In particular, the injection needle 46 can travel a generally linear path 119 with reduced stress and friction during extension and retraction. A linear path of travel is therefore preferred in certain instances, including where components in the tip section are fragile and susceptible to breakage due to compressive and/or shear forces exerted by the components. In particular, components that extend and retract, such as an injection needle, can rub, break or wear down surfaces and structures it repeatedly comes in contact with.

Figure 12:
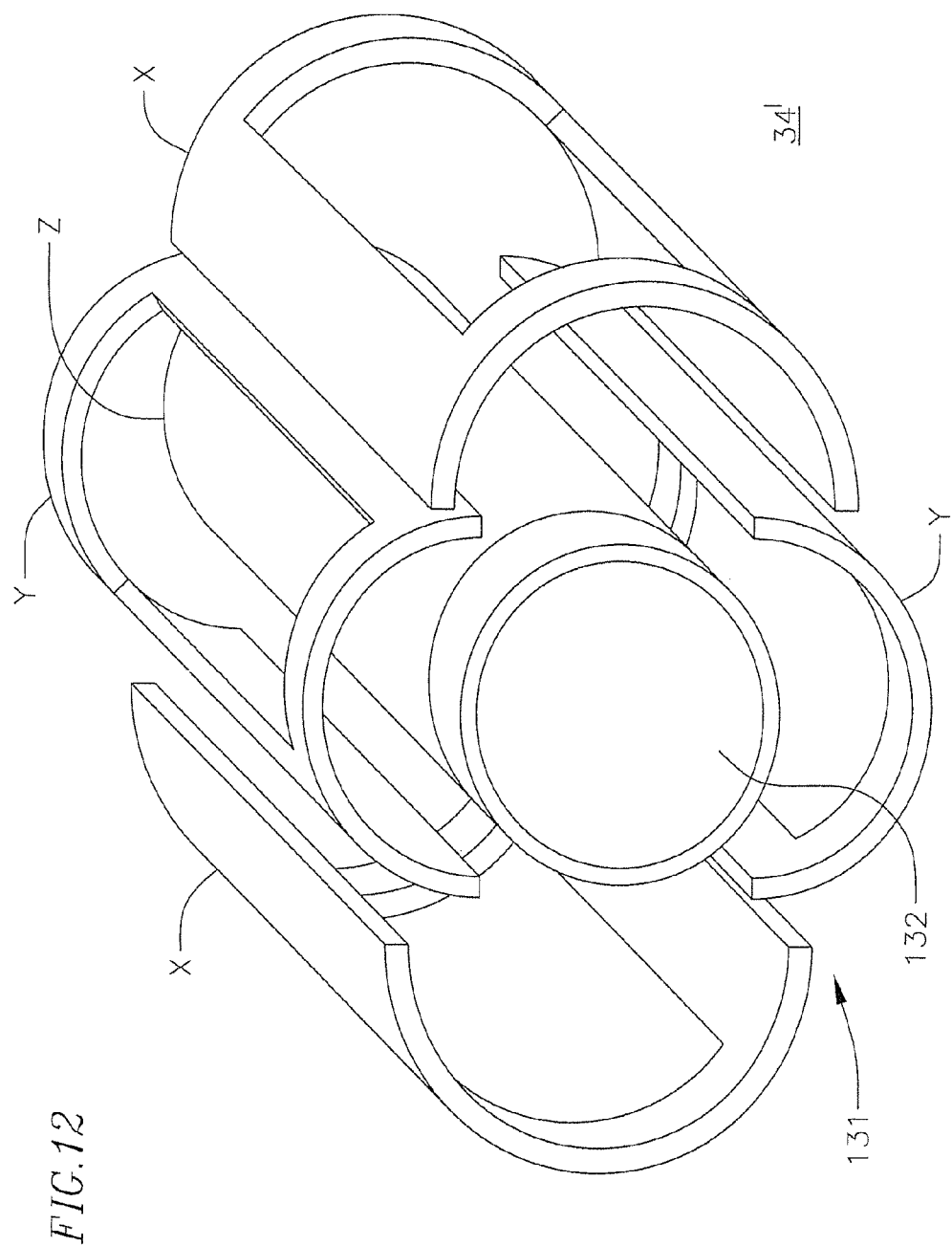
FIG. 12 is an exploded perspective view of an embodiment of a hollow position sensor.

As illustrated in FIG. 12. the position sensor 34' has a generally cylindrical body 131 that is hollow with an inner passage 132. Like the sensor 34, the sensor 34' is adapted to detect location and orientation for generating coordinate and angular data, (for example, x, y, pitch, roll, yaw). Position sensors of similar hollow designs are disclosed in U.S. Pat. No. 6,484,118, the entire disclosure of which is hereby incorporated by reference.

Figure 11:
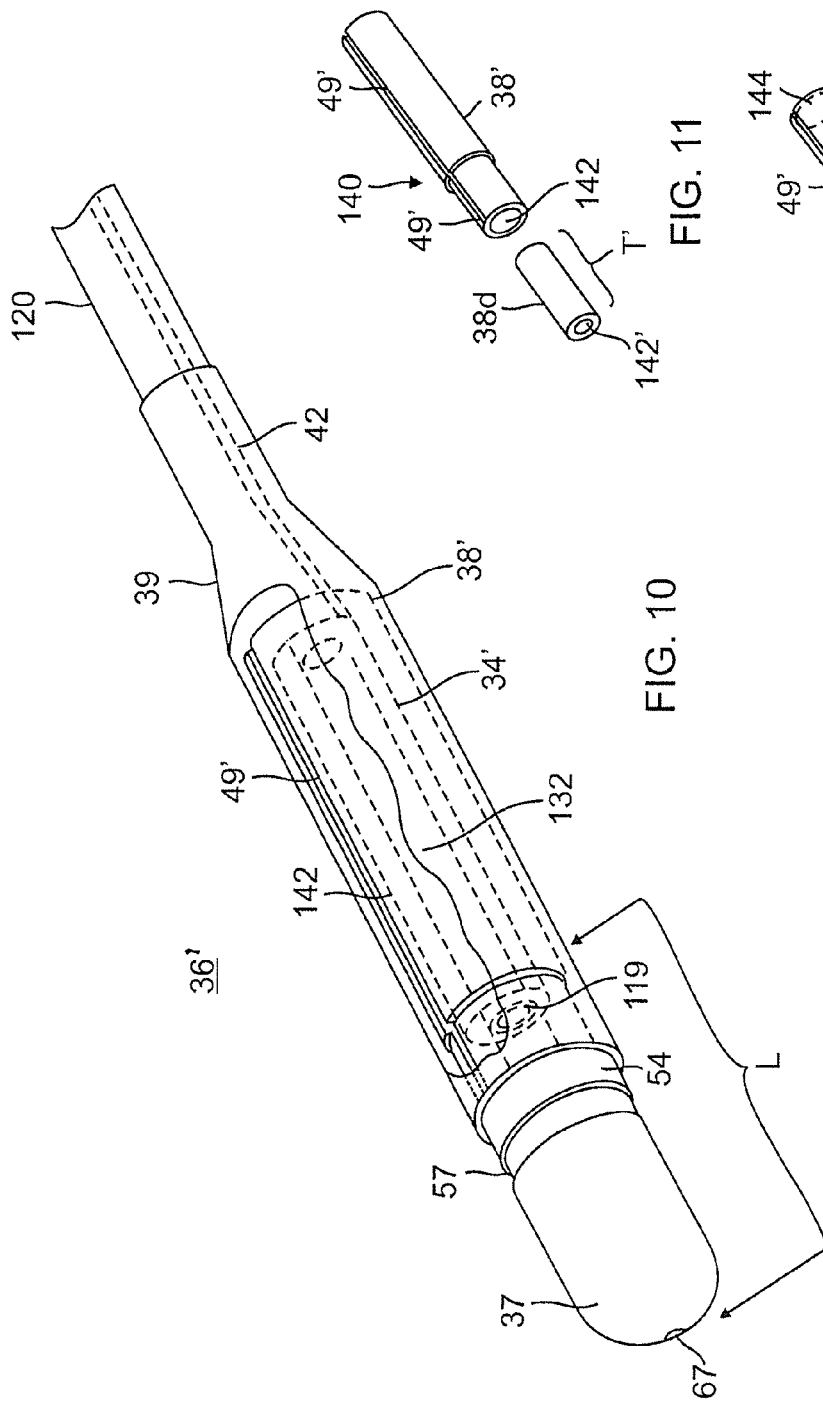
FIG. 11 is a perspective view of an embodiment of the magnetic device of the tip section of FIG. 10.
Figure 13:
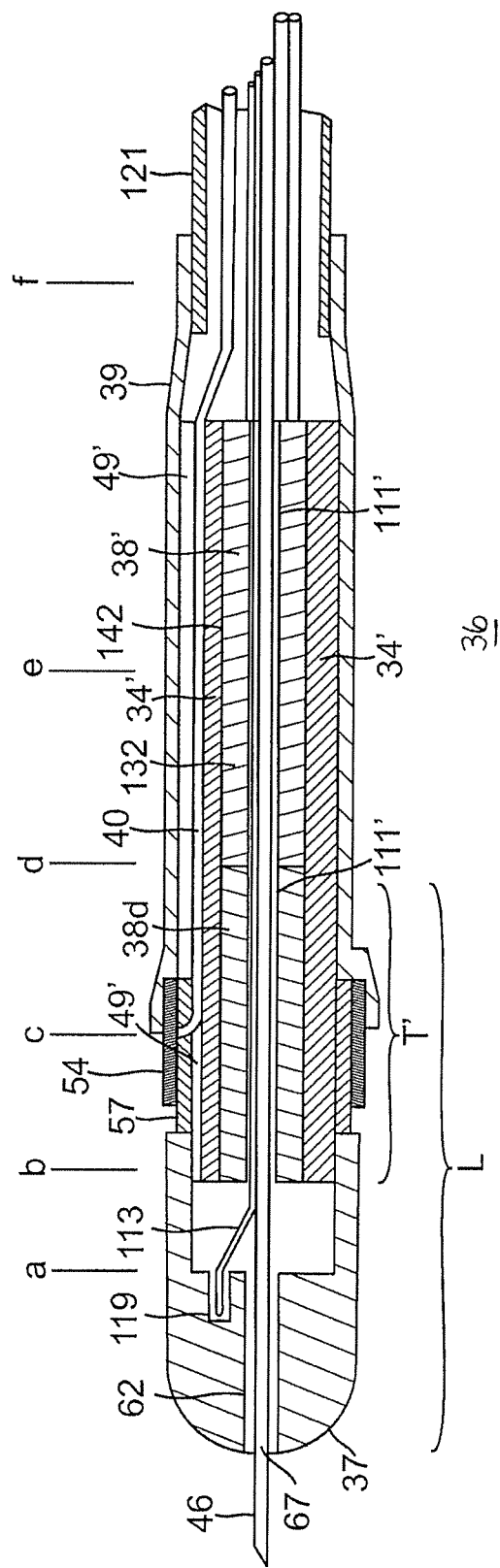
FIG. 13 is a cross-sectional view of the tip section of FIG. 10.
Figure 13A:
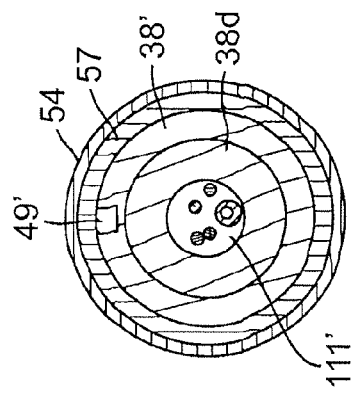
FIG. 13a is a longitudinal cross sectional view of the tip section of FIG. 13, taken along line a-a.
Figure 13B:
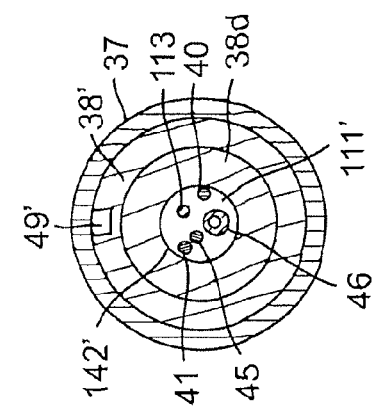
FIG. 13b is a longitudinal cross sectional view of the tip section of FIG. 13, taken along line b-b.
Figure 13C:
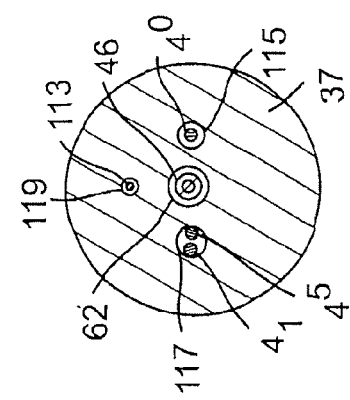
FIG. 13c is a longitudinal cross sectional view of the tip section of FIG. 13, taken along line c-c.
Figure 13F:
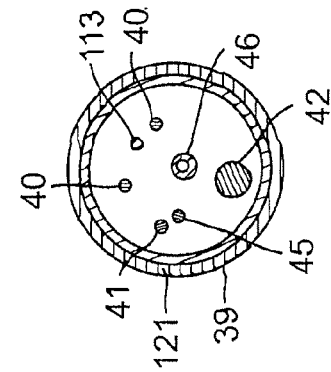
FIG. 13f is a longitudinal cross sectional view of the tip section of FIG. 13, taken along line f-f.
Figure 13E:
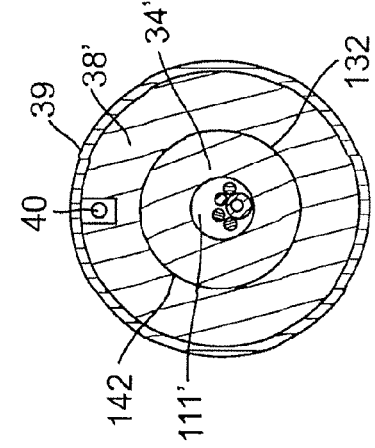
FIG. 13e is a longitudinal cross sectional view of the tip section of FIG. 13, taken along line e-e.
Figure 13D:
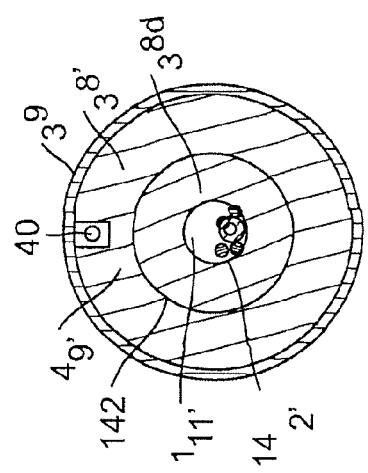
FIG. 13d is a longitudinal cross sectional view of the tip section of FIG. 13, taken along line d-d.

The magnetic device 38' of FIG. 11 also has a generally cylindrical body 140 that is hollow with an inner passage 142. Its outer diameter is sized so that it can sit in the inner passage 132 of the position sensor 34' and when so stacked and assembled, the magnetic device 38' and the position sensor 34' are in a surrounding and circumferential relationship and their respective inner passages 132 and 142 are axially aligned. Components extending between the tip electrode and the intermediate section pass through these inner passages. In particular, concentric inner passages 132 and 142 are on axis with the tip electrode 37 and therefore axially-aligned with the needle duct 62 that defines the concentric needle port 67, as shown in FIG. 13. As such, the injection needle 46 travels a generally linear, on-axis path 111' with minimal stress and friction during extension and retraction. In the illustrated embodiment, the injection needle travels the entire length of path 111' in the tip section.

To ensure that the distal end of the sensor 34 is at the predetermined distance L from the distal end of the tip electrode and that the tip section 36 carries the predetermined volume of magnetic material, the magnetic device includes a magnetic spacer 38d that slides into the distal end of the magnetic device 38'. The spacer has a predetermined length T' such that when its distal end is flush with the distal end of the magnetic device 38', the proximal end of the spacer 38d functions as a stop against which the distal end of the sensor abuts for the proper distance L to the distal end of the tip electrode (see FIG. 13). The spacer also has an inner passage 142' so that components can extend through it.

As illustrated in FIG. 11, the magnetic device can be formed with an integrated spacer as a monolithic piece 38" where a smaller drill bit forms a smaller inner passage 143 in the distal portion and a larger drill bit forms a larger inner passage 144 in the proximal portion such that a stop 151 is formed at the junction of the smaller and larger inner passages.

The lead wire 40 for the tip electrode, the safety wire 113, and the injection needle 46 each travel along the linear path 111' through the hollow position sensor 34' and the hollow magnetic device 38' with the exception of the lead wire 40 for the ring electrode 54 which travels along an outer channel 49' formed along the length of the magnetic device 38' and 38". The channel may be formed by electrical discharge machining (EDM) or any other suitable process.

In the illustrated embodiment of FIGS. 10-13, the hollow position sensor and magnetic device are in a surrounding or circumferential relationship with the position sensor in the interior of the magnetic device. It is understood by one of ordinary skill in the art that the position can also be reversed, with the magnetic device being on the interior of the position sensor. Since both have hollow configurations, either one can be stacked on or slid over the other depending on their diameter. A transitional section 120 with additional magnetic devices can also be connected to the tip section 36'.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the members and components may be sized different in that the drawings are not necessarily to scale. Also, components extending through the catheter may have an overtubing or sheath for insulation and/or protection. The magnetic device and the position sensor may be configured differently but nevertheless be integrated with each other in the tip section. Moreover, the catheter can be adapted for irrigation to cool tissue during ablation. The catheter can also be structured without any control handle where manipulation and control of the catheter and extension, retraction and injection of the needle are automated and/or accomplished remotely.

It is also understood that while the catheter of the present invention is described with ablation, mapping and injection capabilities, ablation need not be included. For example, an injection catheter having an electromagnetic sensor and electrophysiology mapping electrodes may be used in combination with a separate ablation catheter system.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
 a catheter body;
 an intermediate section distal of the catheter body; and
 a tip section distal of the intermediate section, the tip section having a tip electrode with an omnidirectional distal tip and a concentric needle port, the tip section also having a modular magnetic device and a position sensor, the modular magnetic device comprising a distal magnetic member, a mid magnetic member, and a proximal magnetic member, at least a portion of at least one of the distal magnetic member, the mid magnetic member and the proximal magnetic member being in a surrounding relationship with the position sensor;
 a needle extending through the catheter body, the intermediate section and the tip section; and
 a needle control handle adapted to extend and retract the injection needle through the concentric needle port.

2. A catheter of claim 1, wherein the mid magnetic member of the magnetic device includes a hollow portion and the position sensor is positioned at least partially within the hollow portion of the mid member of the magnetic device.

3. The catheter of claim 1, wherein each of the mid magnetic member, the distal magnetic member and the proximal magnetic member have a generally cylindrical configuration, and when assembled, the distal magnetic member, the mid magnetic member and the proximal magnetic member define a path between the tip electrode and the intermediate section through which at least one component can pass and circumvent the position sensor.

4. A catheter of claim 3, wherein the path is in communication with the concentric needle port.

5. A catheter of claim 3, wherein the at least one component is the needle.

6. A catheter of claim 3, wherein the at least one component is a lead wire, a thermocouple wire, an electromagnetic sensor cable, an irrigation tube and/or a tip electrode safety wire.

7. A catheter comprising:
a catheter body;
an intermediate section distal of the catheter body;
a tip section distal of the intermediate section, the tip section having a tip electrode with an omnidirectional distal end and a concentric needle port, the tip section also having a magnetic device and a position sensor, both the magnetic device and the position sensor having a hollow configuration such that one of the magnetic device and the position sensor is received in at least a portion of the other of the magnetic device and the position sensor.

8. The catheter of claim 7, wherein the hollow configuration of the magnetic device and the hollow configuration of the position sensor define a generally linear path between the tip electrode and the intermediate section through which at least one component can pass.

9. The catheter of claim 8, wherein the generally linear path is in communication and alignment with the concentric needle port.

10. The catheter of claim 7, wherein:
the hollow configuration of the position sensor comprises a generally cylindrical sensor body having a hollow interior passage;
the hollow configuration of the magnetic device comprises a generally cylindrical magnetic body having a hollow interior passage; and
either:
the position sensor is received in at least a portion of the interior passage of the generally cylindrical magnetic body of the magnetic device, or
the magnetic device is received in at least a portion of the interior passage of the generally cylindrical sensor body of the position sensor.

11. The catheter of claim 10, wherein the interior passage of the generally cylindrical magnetic body and the interior passage of the generally cylindrical sensor body are axially aligned.

12. The catheter of claim 11, wherein the interior passage of the generally cylindrical magnetic body and the interior passage of the generally cylindrical sensor body are axially aligned with the concentric needle port.

13. The catheter of claim 1, wherein the mid magnetic member comprises a generally C-shaped cross section, an outer diameter, a generally cylindrical inner cavity, and an outer channel.

14. The catheter of claim 13, wherein the position sensor and the proximal magnetic member are both at least partially received in the generally cylindrical inner cavity of the mid magnetic member.

15. The catheter of claim 1, wherein the distal magnetic member comprises a proximal portion and a neck portion, the proximal portion configured to abut a distal end of the mid magnetic member, and the neck portion configured to be received in a proximal end of the tip electrode.

16. The catheter of claim 15, wherein the distal magnetic member further comprises a notch along its length such that both the proximal portion and the neck portion have crescent shaped cross sections.

17. The catheter of claim 16, wherein the distal magnetic member further comprises an inclined channel having proximal and distal ends, the distal end of the inclined channel being deeper in the distal magnetic member than the notch, and the proximal end of the inclined channel being of generally even depth in the distal magnetic member with the notch.

18. The catheter of claim 1, wherein the position sensor is in the generally surrounding relationship with the mid magnetic member, and the position sensor is situated generally between the proximal magnetic member and the distal magnetic member.

19. The catheter of claim 1, wherein the proximal magnetic member has an inner passage through which a component can extend.

20. The catheter of claim 17, wherein:
the mid magnetic member comprises a generally C-shaped cross section, an outer diameter, a generally cylindrical inner cavity, and an outer channel; and
the distal magnetic member is aligned with the mid magnetic member such that the inclined channel and notch of the distal magnetic member are generally aligned with the outer channel of the mid magnetic member.

* * * * *